United States Patent
Rudolph et al.

(10) Patent No.: US 6,310,101 B1
(45) Date of Patent: Oct. 30, 2001

(54) TREATMENTS USING VENLAFAXINE

(75) Inventors: Richard L. Rudolph, Berwyn; Albert T. Derivan, Villanova; Eric A. Muth, New Hope; G. Virginia Upton, Radnor, all of PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/285,812

(22) Filed: Apr. 2, 1999

Related U.S. Application Data

(62) Division of application No. 08/835,780, filed on Apr. 8, 1997, now Pat. No. 5,916,923, which is a continuation of application No. 08/368,521, filed on Jan. 4, 1995, now abandoned, which is a continuation of application No. 08/083,848, filed on Jun. 28, 1993, now abandoned.

(51) Int. Cl.$^7$ .................................................. A61K 31/135
(52) U.S. Cl. .............................................................. 514/649
(58) Field of Search ............................................ 514/648

(56) References Cited

U.S. PATENT DOCUMENTS

| | | | |
|---|---|---|---|
| 4,535,186 | 8/1985 | Husbands et al. | 564/336 |
| 4,609,758 | 9/1986 | Husbands | 564/348 |
| 4,611,078 | 9/1986 | Husbands et al. | 558/410 |
| 4,761,501 | 8/1988 | Husbands et al. | 564/167 |
| 4,824,868 | 4/1989 | Watthey | 514/651 |
| 4,956,388 | 9/1990 | Robertson et al. | 514/651 |
| 4,996,235 | 2/1991 | Robertson et al. | 514/649 |
| 5,006,525 | 4/1991 | Schaus | 514/232.8 |
| 5,013,761 | 5/1991 | Beedle et al. | 514/650 |
| 5,023,269 | 6/1991 | Robertson et al. | 514/438 |
| 5,057,515 | 11/1991 | Schaus | 514/232.8 |
| 5,135,947 | 8/1992 | Robertson et al. | 514/466 |

FOREIGN PATENT DOCUMENTS 0449562   3/1991   (EP) .

OTHER PUBLICATIONS

Ira M. Lesser; Psychiatric Annals 21:6; "The Treatment of Panic Disorders: Pharmacologic Aspects"; pp. 341–346, Jun. 1991.*
Fluoxetine—A Review of Its Pharmacodynamic and Pharmacokinetic Properties, and Therapeutic Efficacy in Depressive Illness. Drugs 32: 481–508 (1986).
Serotonergic Mechanisms in the Behavioral Effects of Buspirone and Gepirone. Eison et al., Pharm. Bioch. and Behavior, vol. 24, pp. 701–707, 1986.
Dexfenfluramine—Its Place in Weight Control. Turner, Drugs 39 (Suppl. 3): 53–62, 1990.
Dosing Strategies for Antidepressant Agents. Schatzburg, J. Clin. Psychiatry 52:5 (suppl.), May 1991.
Fluoxetine: A Serotonergic Appetite Suppressant Drug. Fuller and Wong, Drug Development Research 17: 1–15 (1989).

2–Phenyl–2–(1–hydroxycycloalkyl)ethylamine Derivatives: Synthesis and Antidepressant Activity. Yardley et al., J. Med. Chem., 1990, 33.
Venlafaxine: A New Dimension in Antidepressant Pharmacology. Montgomery, J. Clin. Psychiatry 54:3, Mar. 1993.
Dexfenfluramine—A Review of Its Pharmacological Properties and Therapeutic Potential in Obesity, McTavish et al., Drigs 43(5): 713–733, 1992.
Appetite Suppressants—A Review. Silverstone, Drugs 43(6): 820–836, 1992.
Fontana et al., Psychopharmacology, 95:147–150 (1988).
Bodnoff et al., Psychopharmacology, 97:277–279 (1989).

(List continued on next page.)

Primary Examiner—Theodore J. Criares
Assistant Examiner—Jennifer Kim
(74) Attorney, Agent, or Firm—Rebecca R. Barrett

(57) ABSTRACT

This invention provides a method of treating obesity, generalized anxiety disorder, post-traumatic stress disorder, late luteal phase disphoric disorder (premenstrual syndrome), attention deficit disorder, with and without hyperactivity, Gilles de la Tourette syndrome, bulimia nervosa or Shy Drager Syndrome in a mammal by administering to the mammal an effective amount of a hydroxycycloalkanephenethyl amine of the following structural formula:

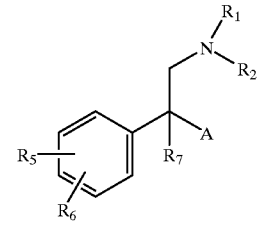

in which A is a moiety of the formula

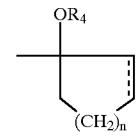

where
  the dotted line represents optional unsaturation;
  $R_1$ is hydrogen or alkyl;
  $R_2$ is alkyl;
  $R_4$ is hydrogen, alkyl, formyl, or alkanol;
  $R_5$ and $R_6$ are, independently, hydrogen, hydroxyl, alkyl, alkoxy, alkanoyloxy, cyano, nitro, alkylmercapto, amino, alkylamino, dialkylamino, alkanamido, halo, trifluoromethyl, or taken together, methylene dioxy;
  $R_7$ is hydrogen or alkyl; and
  n is 0, 1, 2, 3, or 4;
or a pharmaceutically acceptable salt thereof.

19 Claims, No Drawings

OTHER PUBLICATIONS

Bodnoff et al., Psychopharmacology, 95:298–302 (1988).
Lydiard, J. Clin. Psychiatry, 52:6(suppl), Jun. 1991.
Rickels, et al., Arch. Gen. Psychiatry, vol. 50, Nov. 1993.
Kahn, et al., Arch. Gen Psychiatry, vol. 43, Jan. 1986.
Fonzo, et al., Acta Psychiatr Scand, 95:444–450, 1997.
Davies et al., The Journal of Nervous and Mental Disease, vol. 183, No. 1, 1995.
Rickels, et al., J. Clin. Psychiatry, 54:1 (suppl), Jan. 1993.
Anderson, et al., Am. J. Psychiatry 141:4, Apr. 1984.
Barlow, et al., Am. J. Psychiatry, 143:1, Jan. 1986.
Kahn, et al., Journal of Affective Disorders, 13, 145–151 (1987).
Brown, et al., Am. J. Psychiatry, 151:9, Sep. 1994.
Sanderson et al., The Journal of Nervous and Mental Disease, vol. 178, No. 9, 1990.
Wingerson et al., J. Clin. Psychopharmacology, vol. 12, No. 3, Jun. 1992.
Wilcox et al., Prog. Neuro–Psychopharmacol. & Biol. Psychiat, vol. 18, 979–993, 1994.
Hoehn–Saric et al., J. Clin. Psychiatry 49:8, Aug. 1988.
Shores et al., Comprehensive Psychiatry, vol. 33, No. 4, 237–244, 1992.
Rickels et al., JAMA, vol. 250, No. 6, Aug. 12, 1983.
Rickels et al., Arch. Gen. Psychiatry, vol. 45, May 1988.
Rickels et al., J. Clin. Psychopharmacology, vol. 10, No. 3, 1990.

* cited by examiner

TREATMENTS USING VENLAFAXINE

This application is Division of U.S. Ser. No. 08/835,780 filed Apr. 8, 1997 now patented as U.S. Pat. No. 5,916,923; which is a continuation of application Ser. No. 08/368,521, filed Jan. 4, 1995 now abondoned; which is a a continuation of application Ser. No. 08/083,843, filed Jun. 28, 1993, now abondoned.

BACKGROUND OF THE INVENTION

The active ingredients of this invention include (1-[2-(dimethylamino)-1-(4-methoxyphenyl)ethyl] cyclohexanol), or therapeutically acceptable salts thereof, which are known generally as venlafaxine and its analogues. Venlafaxine is disclosed in U.S. Pat. No. 4,535,186 (Husbands et al.) and has been previously reported to be useful as an antidepressant. U.S. Pat. No. 4,535,186 teaches the production of venlafaxine and its analogues and is incorporated herein as reference. For the purposes of this disclosure, and the claims that follow, the use of venlafaxine is understood to include the free base and pharmaceutically acceptable salt forms of venlafaxine, the racemate and its individual enantiomers, and venlafaxine analogs, both as racemates and as their individual enantiomers.

Venlafaxine has been shown to be a potent inhibitor of monoamine neurotransmitter uptake, a mechanism associated with clinical antidepressant activity. Due to its novel structure, venlafaxine has a mechanism of action unrelated to other available antidepressants, such as the tricyclic antidepressants desipramine, nostrptyline, protriptyline, imipramine, amitrptyline, trimipramine and doxepin.

It is believed that venlafaxine's mechanism of action is related to potent inhibition of the uptake of the monoamine neurotransmitters serotonin and norepinephrine. To a lesser degree, venlafaxine also inhibits dopamine reuptake, but it has no inhibitory activity on monoamine oxidase. O-desmethylvenlafaxine, venlafaxine's major metabolite in humans, exhibits a similar pharmacologic profile. Venlafaxine's ability to inhibit norepinephrine and serotonin (5-HT) uptake has been predicted to have an efficacy which rivals or surpases that of tricyclic antidepressants (Stuart A. Montgomery, M.D., J. Clin. Psychiatry, 54:3, March 1993).

In contrast to classical tricyclic antidepressant drugs, venlafaxine has virtually no affinity for muscarinic, histaminergic or adrenergic receptors in vitro. Pharmacologic activity at these receptors is associated with the various anticholinergic, sedative and cardiovascular effects seen with the tricyclic antidepressant drugs.

DESCRIPTION OF THE INVENTION

In accordance with the present invention there is provided a method of treating, preventing, or controlling obesity, panic disorder, post-traumatic stress disorder, late luteal phase dysphoric disorder (premenstrual syndrome), attention deficit disorders, with and without hyperactivity, Gilles de la Tourette syndrome, bulimia nervosa, generalized anxiety disorder or Shy Drager Syndrome in mammals, preferably in humans. Each of these disorders exhibit a physiological basis for treatment by venlafaxine's ability to inhibit monoamine neurotransmitters.

There is increasing evidence from animal studies that serotonin has an inhibitory role in the control of food intake and modern drug therapy suggests that serotonin is involved in appetite and mood. Both children and adults increase their appetite and gain weight when treated with cvproheptadine, a serotonin receptor blocker. By inhibiting serotonin reuptake, venlafaxine and its analogues can increase synaptic serotonin (5-hydroxytriptamine, 5-HT) and induce anorexia. This action serves as a treatment for obesity.

Bulimia Nervosa is characterized by recurrent binge eating in which the individual feels a loss of control over eating and regularly practices rigorous dieting or fasting, or purging by self-induced vomiting, or the use of diuretics, or laxatives in an attempt to overcome the feeling. Eating binges are generally episodic and may be triggered by psvchosocial stress and may occur as often as several times a day. As an antidepressant. venlafaxine can be used to reduce the frequency of binging and purging in both depressed and nondepressed bulimics.

Several links exist between late luteal phase dvsphoric disorder (LLPDD) and major depression, including similar clinical features and an increased lifetime prevalence of major depression in women with LLPDD. In addition, women with confirmed LLPDD have demonstrated abnormalities in premenstrual levels of serotonin. Premenstrual carbohydrate craving and increased carbohydrate intake in patients with this condition are also suggestive of serotonin involvement. Venlafaxine and its analogues are effective in treating LLPDD because of their serotonin uptake inhibitory ability.

Similarly, the antidepressant activity of venlafaxine and its analogues can be used in the treatment of attention deficit disorders (ADD), with and without hyperactivity, which is characterized by strong behavioral abnormalities. ADD occurs in between 3 and 10% of school age children and is one of the most common childhood and adolescent psychiatric conditions. At the present time, there are three hypotheses suggesting that deficits or dysregulation of the monoamine neurotransmitter system exists in ADD, specifically deficits in noradrenergic, dopaminergic and serotonergic neuronal systems.

Psychopharmacological treatment has proven beneficial in many patients with ADD. The psychotropics most commonly used have come from two different medication groups, the psychostimulants and antidepressants. Imipramine and desipramine have been most commonly prescribed for the treatment of ADD, though fluoxetine has also been used.

One related disorder of interest to the present invention is Gilles de la Tourette syndrome, which is often referred to as Tourette syndrome or Tourette's syndrome. The malady may begin with simple tics, but can progress to multiple, complex movements, which may include vocal and respiratory tics. The vocal tics associated with the syndrome may include grunting or barking noises or may amount to compulsive utterances, often including involuntary curses or derozatory remarks. Agents currently used in the treatment of Tourette syndrome include benzodiazepine anxiolytics, such as lorazepam, for simple tics and haloperidol, clonidine or pimozide for more advanced cases of the syndrome.

Generalized Anxiety Disorder is a syndrome characterized by excessive or chronic anxiety or apprehension concerning two or more of life's circumstances. The disorder's signs and symptoms often include somatic complaints, such as tremor, dyspnea, palpitations, lightheadedness, and nausea.

Acute anxiety attacks (panic disorders) are a defining symptom of anxiety neurosis and are extremely unpleasant for the patient who experiences a subjective fear which arises for no apparent reason. This fear may be a fear of some imminent castastrophe which prevents rational reasoning.

Such anxiety disorders have been treated by a combination of psychologic and pharmocologic measures. Psychologic treatments may include insight psychotherapy, supportive psychotherapy and relaxation techniques, such as meditation or hypnosis. Pharmocologic treatments include those medications that lower the stress level of the patient. Minor tranquilizers are used for controlling the symptoms of chronic or anticipatory anxiety. Panic attacks can be prevented or reduced in severity by therapeutic doses of antidepressants, including venlafaxine and other serotonin reuptake inhibitors, tricyclic antidepressant medications or monoamine oxidase inhibitors.

Venlafaxine and its analogues can also be used to treat Post Traumatic Stress Disorder (PTSD), which may develop after exposure to severe stresses, such as combat, accident, assaults and natural disasters. PTSD is characterized by symptoms of hyperalertness, sleep disturbance, survivor guilt, impairment of concentration and memory, avoidance of reminders and recollection of traumatic events, intensive daydreams or images, and recurrent nightmares.

While treatment for PTSD consists largely of relaxation techniques designed at relieving the hyperarousal and anxiety symptoms, antidepressants, including serotonin uptake inhibitors, assist in patient recovery.

Venlafaxine and its analogues can also be used as a part of a medical regimen associated with Shy-Drager Syndrome (SDS), which is a multiple systems degeneration resulting in widespread neurologic damage. Autonomic dysfunction with cerebellar ataxia, parkinsonism, corticospinal and corticobulbar trost dysfunction, and amyotrophy are known to occur. The cause of SDS is unknown and its course is progressive. Severe disability or death usually occurs within five to ten years after onset, often from bulbar dysfunction and/or laryngeal stridor.

The methods of the present invention involve administering to a mammal in need thereof an effective amount of one or more compounds from a group of substituted phenethylamines. The compounds of this invention present the following structural formula:

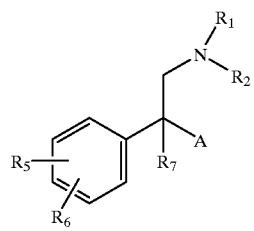

in which A is a moiety of the formula

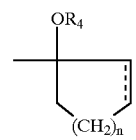

where
the dotted line represents optional unsaturation;
$R_1$ is hydrogen or alkyl of 1 to 6 carbon atoms;
$R_2$ is alkyl of 1 to 6 carbon atoms;
$R_4$ is hydrogen, alkyl of 1 to 6 carbon atoms, formyl, or alkanol of 2 to 7 carbon atoms;
$R_5$ and $R_6$ are independently hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkyl amino of 1 to 6 carbon atoms, dialkylamino in which each alkyl group is of 1 to 6 carbon atoms, alkanamido of 2 to 7 carbon atoms, halo, trifluoromethyl, or when taken together, methylene dioxy;
$R_7$ is hydrogen or alkyl of 1 to 6 carbon atoms; and n is one of the integers 0, 1, 2, 3, or 4;
or a pharmaceutically acceptable salt thereof.

The preferred compounds are those of the formula:

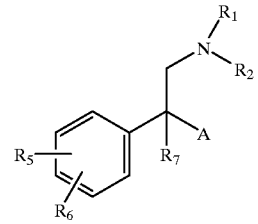

in which
A is as defined supra;
$R_1$ is hydrogen or alkyl of 1 to 3 carbon atoms;
$R_2$ is alkyl of 1 to 3 carbon atoms;
$R_5$ is hydrogen, hydroxyl, alkoxy of 1 to 3 carbon atoms, chloro, bromo, trifluoromethyl or alkyl of 1 to 3 carbon atoms;
$R_6$ is alkyl of 1 to 3 carbon atoms, alkoxy of 1 to 3 carbon atoms, chloro, bromo, trifluoromethyl or alkanoyloxy of 2 to 3 carbon atoms;
$R_7$ is hydrogen or alkyl of 1 to 3 carbon atoms; or a pharmaceutically acceptable salt thereof.

The most preferred compounds are those in which $R_5$ and $R_6$ are both in the meta positions or one of $R_5$ or $R_6$ is in the para position and n is 2.

Of particular interest are the compounds 1-[(2-dimethylamino)-1-(4-methoxyphenyl)ethyl]cyclohexanol and 1-[(2-dimethylamino)-1-(4-hydoxyphenyl)ethyl] cyclohexanol and the enantiomers and pharmaceutically acceptable salts thereof.

The compounds in which R4 is formyl or alkanoyl of 2 to 7 carbon atoms have been found to be not as potent as the corresponding free hydroxy bearing derivatives. However, in long term therapy the acyloxy derivatives will act as pro drugs as the acyl group is removed in vivo either via acid hydrolysis in the stomach or enzymatically.

The pharmaceutically acceptable acid addition salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic and similar acids. For parenteral administration, the use of water soluble salts is preferred, although either the free base of the pharmaceutically acceptable salts are applicable for oral or parenteral administration of the antidepressant agents of this invention. The halo substituent representing $R_5$ or $R_6$ is intended to include the chloro, bromo, iodo or fluoro substituents.

Pharmaceutical compositions containing the compounds of this invention represent an additional aspect of this invention. The active ingredient can be compounded into any of the usual oral dosage forms including tablets, capsules and liquid preparations such as elixirs and suspensions containing various coloring, flavoring, stabilizing and flavor masking substances. For compounding oral dosage forms, the active ingredient can be mixed with various conventional tabletting materials such as starch, calcium carbonate, lactose, sucrose and dicalcium phosphate to aid the tabletting or capsulating process. Magnesium stearate, as an additive, provides a useful lubricant function when desired.

The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene lycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilized by intramuscular, intraperitoneal or subcutaneous injection.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be varied or adjusted from 2 mg. or less to 50 mg. or more, according to the particular need and the activity of the active ingredient. The usual oral recommended dose of venlafaxine for humans may be between about 75 and about 200 mg/day and this dose may be administered in two or three divided doses, preferably with food if administered orally. A maximum recommended daily dose for humans would be about 375 mg, but it will be understood by one skilled in the art that dosage under this invention will be determined by the particular circumstances surrounding each case.

One skilled in this art will also be aware that the routes of administering the compounds of this invention may vary significantly. In addition to other oral administrations, sustained release compositions may be favored. Other acceptable routes may include, but are not limited to, intravenous, intramuscular and intraperitoneal injections, subdermal implants, as well as buccal, sublingual, transdermal, topical, rectal, vaginal and intranasal administrations. Bioerodible, non-bioerodible, biodegradable and non-biodegradable systems of administration may also be used.

It should also be understood that the present invention is intended to include all methods of, and reasons for, treating obesity, panic disorder, post-traumatic stress disorder, late luteal phase dysphoric disorder (premenstrual syndrome), attention deficit disorders, with and without hyperactivity, Gilles de la Tourette syndrome, bulimia nervosa, generalized anxiety disorder or Shy Drager Syndrome in mammals, preferably in humans. For the purposes of this invention, treating these maladies and disorders is to be understood as including all prophylactic, therapeutic, progression inhibiting, remedial, maintenance, curative or other treatments, regimens or administrations of or with venlafaxine that yield the desired effects in the mammal receiving venlafaxine.

The following example is provided to demonstrate the use of venlafaxine in the treatment of obesity. This example is merely illustrative and does not limit the scope of the present invention.

Obesity Reduction Test

A randomized double-blind comparison of venlafaxine and placebo capsules was tested as a treatment for obesity in non-depressed outpatients. The test was conducted over a period of ten (10) weeks with 98 people between the ages of 18 and 65 receiving double-blind medication (50 receiving venlafaxine and 48 receiving a placebo). Each participant in the comparison weighed more than 20%, but less than 100%, above the mean value for sex, height and bone structure according to the 1983 Metropolitan Height and Weight Table. The women in the comparison of childbearing potential received a negative pregnancy test result and agreed to use medically acceptable forms of contraception throughout the period covered by the comparison.

The initial venlafaxine dose was 25 mg at bedtime on study day 1. Subsequently the dose was increased from 50 mg/day to 150 mg/day through study day 14. On study day 15 the dose was increased to 225 mg/day (3 tablets 3 times a day) and this dose was continued for the remainder of the 70 day study. The patients in both groups were also given instructions to decrease their food intake by 20% and to increase their exercise by the same amount. These directives were given to standardize dietary instructions and to try to prevent patients from starting "crash" diets or exercise programs. A specific diet was not prescribed.

Comparisons within groups were performed on changes from baseline weight and body mass index. Body mass index was computed according to the following formula:

$$\text{Body Mass Index} = \frac{Weight \text{ (lb.)} \times 100}{Height \text{ (in.)} \times Height \text{ (in.)}}$$

Obesity Reduction Test Results

The venlafaxine group showed consistent statistically significant mean weight decreases and mean percent decreases from baseline beginning at week 1. Overall, the mean decrease in body weight for the venlafaxine group at week 10 was 7.5 lb with a mean percent decrease from baseline of 3.6%. In contrast, the mean decrease in body weight for the placebo group at week 10 was 1.3 lb with a mean percent decrease from baseline of 0.7%. The body mass index evaluation for the venlafaxine also showed a pattern of decreases similar to that of the weight decreases.

What is claimed is:

1. A method of treating panic disorder, in a mammal suffering from panic disorder, comprising administering to the mammal an effective amount of a compound of the formula:

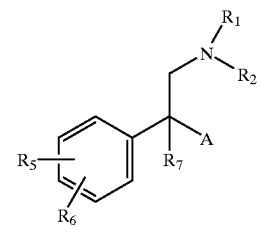

in which A is a moiety of the formula

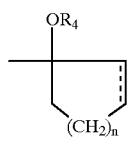

wherein
   the dotted line represents optional unsaturation;
   R1 is hydrogen or alkyl of 1 to 6 carbon atoms;
   $R_2$ is alkyl of 1 to 6 carbon atoms;
   $R_4$ is hydrogen, alkyl of 1 to 6 carbon atoms, formyl, or alkanol of 2 to 7 carbon atoms;
   $R_5$ and $R_6$ are, independently, hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or taken together, methylene dioxy;
   $R_7$ is hydrogen or alkyl of 1 to 6 carbon atoms; and
   n is 0, 1, 2, 3, or 4;
or a pharmaceutically acceptable salt thereof.

2. The method of claim 1 wherein the compound is:

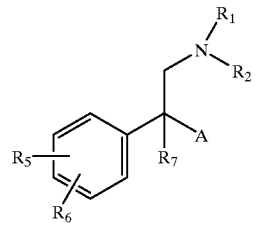

in which A is a moiety of the formula

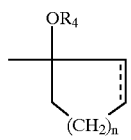

wherein
   the dotted line represents optional unsaturation, and
   $R_1$ is hydrogen or alkyl of 1 to 3 carbon atoms;
   $R_2$ is alkyl of 1 to 3 carbon atoms;
   $R_5$ is hydrogen, hydroxyl, alkoxy of 1 to 3 carbon atoms, chloro, bromo, trifuoromethyl or alkyl of 1 to 3 carbon atoms;
   $R_6$ is alkyl of 1 to 3 carbon atoms, alkoxy of 1 to 3 carbon atoms, chloro, bromo, trifluoromethyl or alkanoyloxy of 2 to 3 carbon atoms;
   $R_7$ is hydrogen or alkyl of 1 to 3 carbon atoms;
or a pharmaceutically acceptable salt thereof.

3. The method of claim 2 wherein $R_5$ and $R_6$ are both in the meta positions or one of $R_5$ or $R_6$ is in the para position and n is 2.

4. The method of claim 2 wherein the compound is 1-[(2-dimethylamino)-1-(4-methoxyphenyl)ethyl]cyclohexanol or a pharmaceutically acceptable salt thereof.

5. The method of claim 2 wherein the compound is 1-[2-(dimethylamino)-1-(4-hydroxyphenyl)ethyl]cyclohexanol or a pharmaceutically acceptable salt thereof.

6. The method of claim 1 wherein the effective amount comprises a daily dose of between about 50 mg/day and about 375 mg/day.

7. The method of claim 4 wherein the effective amount comprises a daily dose of between about 75 mg/day and about 200 mg/day.

8. A method of treating panic disorder in a human, comprising administering to the human in need thereof an effective amount of a compound of the formula:

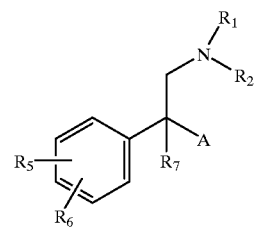

in which A is a moiety of the formula

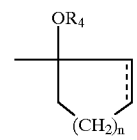

wherein
   the dotted line represents optional unsaturation;
   R1 is hydrogen or alkyl of 1 to 6 carbon atoms;
   $R_2$ is alkyl of 1 to 6 carbon atoms;
   $R_4$ is hydrogen, alkyl of 1 to 6 carbon atoms, formyl, or alkanol of 2 to 7 carbon atoms;
   $R_5$ and $R_6$ are, independently, hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or taken together, methylene dioxy;
   $R_7$ is hydrogen or alkyl of 1 to 6 carbon atoms; and
   n is 0, 1, 2, 3, or 4;
or a pharmaceutically acceptable salt thereof.

9. A method of treating panic disorder in a human, the method comprising administering to a human in need thereof a pharmaceutical composition comprising an effective amount of a compound of the formula:

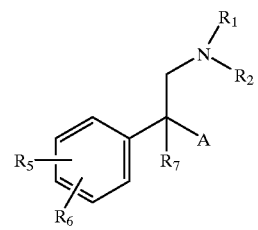

in which A is a moiety of the formula

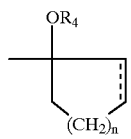

wherein
   the dotted line represents optional unsaturation;
   R1 is hydrogen or alkyl of 1 to 6 carbon atoms;
   $R_2$ is alkyl of 1 to 6 carbon atoms;
   $R_4$ is hydrogen, alkyl of 1 to 6 carbon atoms, formyl, or alkanol of 2 to 7 carbon atoms;
   $R_5$ and $R_6$ are, independently, hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or taken together, methylene dioxy;
   $R_7$ is hydrogen or alkyl of 1 to 6 carbon atoms; and
   n is 0, 1, 2, 3, or 4;
or a pharmaceutically acceptable salt thereof, and a carrier.

10. The method of claim 8 comprising administering to a human in need thereof an effective amount of the compound 1-[(2-dimethylamino)-1-(4-methoxyphenyl)ethyl]cyclohexanol or a pharmaceutically acceptable salt thereof.

11. The method of claim 9 comprising administering to a human in need thereof a pharmaceutical composition containing an effective amount of 1-[(2-dimethylamino)-1-(4-methoxyphenyl)ethyl]cyclohexanol or a pharmaceutically acceptable salt thereof and a carrier.

12. The method of claim 8 wherein the effective amount comprises a daily dose of between about 50 mg/day to about 375 mg/day.

13. The method of claim 8 wherein the effective amount comprises a daily dose of about 75 mg/day to about 200 mg/day.

14. The method of claim 9 wherein the effective amount comprises a daily dose of between about 50 mg/day to about 375 mg/day.

15. The method of claim 9 wherein the effective amount comprises a daily dose of about 75 mg/day to about 200 mg/day.

16. The method of claim 8 comprising administering orally to a human in need thereof an effective amount of the compound 1-[(2-dimethylamino)-1-(4-methoxyphenyl)ethyl]cyclohexanol or a pharmaceutically acceptable salt thereof.

17. The method of claim 9 comprising administering orally to a human in need thereof a pharmaceutical composition containing an effective amount of 1-[(2-dimethylamino)-1-(4-methoxyphenyl)ethyl]cyclohexanol or a pharmaceutically acceptable salt thereof and a carrier.

18. The method of claim 9 wherein the pharmaceutical composition is in tablet form.

19. The method of claim 9 wherein the pharmaceutical composition is in capsule form.

* * * * *

UNITED STATES PATENT AND TRADEMARK OFFICE
Certificate

Patent No. 6,310,101 B1

Patented: October 30, 2001

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Richard L. Rudolph, Berwyn, PA; and Albert T. Derivan, Villanova, PA.

Signed and Sealed this Thirtieth Day of July 2002.

MINNA MOEIZIE
*Supervisory Patent Examiner*
Art Unit 1617